United States Patent
Furui

(10) Patent No.: US 6,577,756 B1
(45) Date of Patent: Jun. 10, 2003

(54) METHOD AND APPARATUS FOR QUANTITATIVELY EVALUATING SCINTILLATION, ANTIGLARE FILM AND METHOD OF PRODUCING THE SAME

(75) Inventor: Gen Furui, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 09/510,506

(22) Filed: Feb. 22, 2000

(30) Foreign Application Priority Data

Feb. 19, 1999 (JP) .......................... 11-041051
Jan. 26, 2000 (JP) .......................... 12-017345

(51) Int. Cl.[7] .................................................. G06K 9/00
(52) U.S. Cl. ...................................... 382/141; 359/615
(58) Field of Search .......................... 382/141; 348/86, 348/125; 700/95, 212; 359/601, 613, 614, 615, 599

(56) References Cited

U.S. PATENT DOCUMENTS 6,131,874 A * 10/2000 Vance et al. ................ 248/550
6,164,785 A * 12/2000 Maekawa .................... 359/613
2002/0034013 A1 * 3/2002 Nakamura et al. .......... 359/603
2002/0122257 A1 * 9/2002 Suga et al. .................. 359/580
2002/0150722 A1 * 10/2002 Suzuki ........................ 428/141

OTHER PUBLICATIONS

"Measurement Technique for Micro Abrasion Anti–Glare", IBM Technical Disclosure Bulletin, Dec. 1982, U.S., No. 25, Issue 7B, P3612–3613.*

* cited by examiner

Primary Examiner—Samir Ahmed
(74) Attorney, Agent, or Firm—Sughrue Mion, PLLC

(57) ABSTRACT

A method capable of quantitatively evaluating the intensity of scintillation caused by surface unevenness. Light from a white light source is made incident on a surface of an object to be measured through a matrix filter. Reflected light or transmitted light from the object is photographed with a CCD camera and taken into a computer as data. Image processing for the luminance distribution of the captured light is performed to obtain a standard deviation of dispersion of the luminance distribution. The value of the standard deviation obtained is defined as a scintillation value of the surface of the object. The performance of the object is evaluated by judging whether or not the scintillation value is greater than a predetermined value.

9 Claims, 5 Drawing Sheets

Captured raw image

Luminance distribution

After image processing

Luminance distribution

Small scintillation

Large scintillation

Luminance distribution

Luminance distribution

FIG. 6

| | Gloss 20° | Sensory test | Scintillation value (present invention) |
|---|---|---|---|
| Sample 1 | 19.4 | × | 24 |
| Sample 2 | 14.3 | ○ | 14 |
| Sample 3 | 7.8 | △ | 17 |
| Sample 4 | 3.8 | ○ | 14 |
| Sample 5 | 26.1 | △ | 16 |
| Sample 6 | 6.3 | ○ | 14 |
| Sample 7 | 2.2 | ◎ | 11 |
| Sample 8 | 7.4 | × | 20 |
| TAC | 59.0 | ◎ | 4 |

METHOD AND APPARATUS FOR QUANTITATIVELY EVALUATING SCINTILLATION, ANTIGLARE FILM AND METHOD OF PRODUCING THE SAME

BACKGROUND OF THE INVENTION

1. Field of the Invention

The present invention relates to a method and apparatus for quantitatively evaluating scintillation caused by surface unevenness. The present invention also relates to an antiglare film and a method of producing the same.

2. Description of Related Art

In display units such as LCDs, a phenomenon known as "scintillation" may occur. This is one of causes that make it difficult for the viewer to see the display. Scintillation is a phenomenon in which when the screen of a display unit is lit up, fine unevenness of luminance appears on the screen, and the position of the luminance unevenness appears to change as the viewing angle is changed. Scintillation is likely to appear particularly when white or green is displayed over the whole screen. Display units need to undergo an evaluation of the degree of such scintillation. The conventional practice is to use a 20-degree specular glossiness measuring method in which the intensity of light regularly reflected from a specimen when light is incident thereon at an angle of 20 degrees is measured. However, scintillation occurs due to surface unevenness or the like. Therefore, scintillation cannot accurately be evaluated by a method in which the intensity of reflected light is measured. Accordingly, a visual evaluation method has heretofore been employed to judge the quality of an antiglare film used to prevent scintillation.

However, it cannot be denied that the visual evaluation of scintillation is likely to cause differences between individuals in the evaluation and lacks accuracy. In development of antiglare films, etc., it has been demanded that the intensity of scintillation should be made capable of being evaluated quantitatively in order to understand the performance of antiglare films, etc.

SUMMARY OF THE INVENTION

To solve the above-described problem, an object of the present invention is to provide a method capable of quantitatively evaluating the intensity of scintillation, which changes with surface unevenness or the like.

Another object of the present invention is to provide an antiglare film superior in scintillation preventing characteristics.

The present invention provides a method of quantitatively evaluating scintillation. According to the evaluation method, light from a white light source is made incident on a surface of an object to be measured through a matrix filter. Reflected light or transmitted light from the object is photographed and captured as data. Image processing is performed for the luminance distribution of the captured light to obtain a standard deviation of the dispersion of the luminance distribution. The value of the obtained standard deviation is defined as a scintillation value of the surface of the object.

The object may be an antiglare film.

The performance of the object may be evaluated by judging whether or not the scintillation value is greater than a predetermined value.

Preferably, the predetermined value for the scintillation value is 15 when the scintillation value is measured at a mean luminance of 145 cd/m$^2$ of the captured image.

In addition, the present invention provides an apparatus for quantitatively evaluating scintillation. The apparatus includes at least a white light source, a matrix filter, a photographing device, and a computer. Light from the white light source is made incident on a surface of an object to be measured through the matrix filter. Reflected light or transmitted light from the object is photographed with the photographing device and captured as data. The data is processed by the computer to obtain a standard deviation of the dispersion of the luminance distribution. The value of the standard deviation thus obtained is defined as a scintillation value of the surface of the object.

In the above-described evaluation apparatus, the photographing device may be a CCD camera.

The object may be an antiglare film.

The performance of the object may be evaluated by judging whether or not the scintillation value is greater than a predetermined value.

Preferably, the predetermined value for the scintillation value is 15 when the scintillation value is measured at a mean luminance of 145 cd/m$^2$ of the captured image.

In addition, the present invention provides an antiglare film whose scintillation value is greater than zero and not greater than 15 when measured at a mean luminance of 145 cd/m$^2$ of a captured image.

In addition, the present invention provides a method of producing an antiglare film having an antiglare layer formed on at least one surface of a base. According to the production method, light from a white light source is made incident on a surface of the antiglare film through a matrix filter. Reflected light or transmitted light from the antiglare film is photographed with a photographing device and captured as data. Image processing is performed for the luminance distribution of the captured light by a computer to obtain a standard deviation of the dispersion of the luminance distribution. The standard deviation thus obtained is defined as a scintillation value of the surface of the antiglare film. The antiglare layer is formed so that the scintillation value is not greater than a predetermined value.

In the above-described production method, the photographing device may be a CCD camera.

Preferably, the predetermined value for the scintillation value is 15 when the scintillation value is measured at a mean luminance of 145 cd/m$^2$ of the captured image.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 6 is a diagram showing the results of measurement.

DESCRIPTION OF THE PREFERRED EMBODIMENTS

Embodiments of the present invention will be described below.

Figure 1:
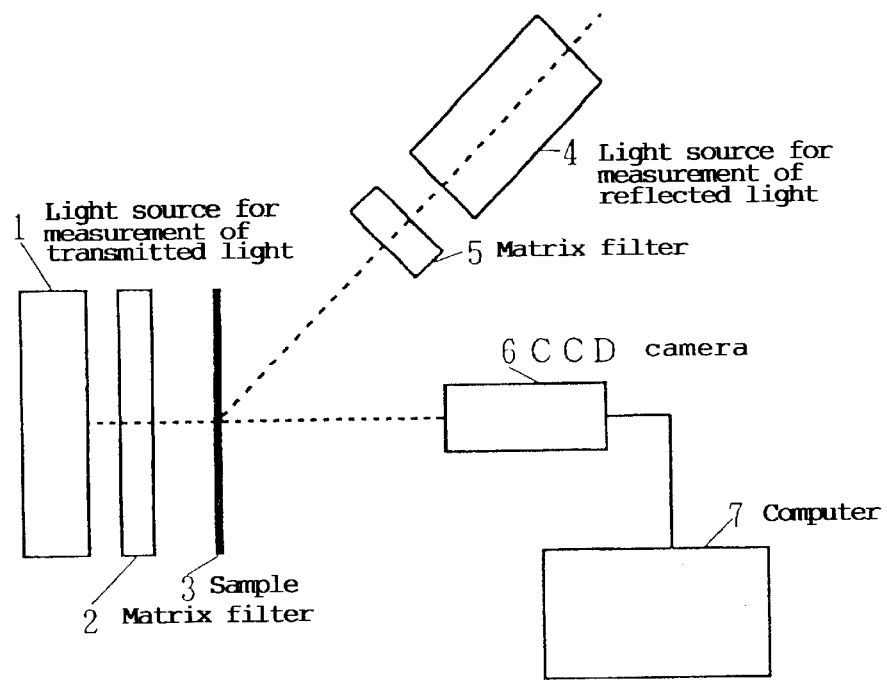
FIG. 1 is a diagram schematically showing the arrangement of an evaluation apparatus according to the present invention.

FIG. 1 is a diagram schematically showing the arrangement of an evaluation apparatus according to the present invention.

The evaluation apparatus has a white light source 1 for measurement of transmitted light. A matrix filter 2 is placed over the white light source 1 with a slight gap therebetween in such a way that the processed surface of the matrix filter 2 faces the white light source 1. An antiglare film (AG film) 3 is brought into close contact with the matrix filter 2 in such a way that an antiglare-treated surface of the antiglare film 3 faces toward the photographing side. Similarly, a white light source 4 for measurement of reflected light is provided, and a matrix filter 5 is placed over the white light source 4 with a slight gap therebetween in such a way that the processed surface of the matrix filter 5 faces the white light source 4. The matrix filter 5 faces the antiglare-treated surface of the antiglare film 3. The antiglare-treated surface of the antiglare film 3 is formed by using a material mainly containing fine particles. The matrix filters 2 and 5 are pseudo color filters each comprising only a black matrix and not colored. Each of the matrix filters 2 and 5 is, for example, a staggered arrangement filter having a length of 85 millimeters, a breadth of 65 millimeters, a thickness of 1 millimeter and a pitch of 140 micrometers×170 micrometers. Although pseudo color filters are used in this embodiment, colored color filters may be used according to need. It should be noted that it is desirable to use a planar white light source as a light source.

The antiglare-treated surface of the antiglare film 3 illuminated with the white light source 1 or 4 through the matrix filter 2 or 5 is photographed with a CCD camera 6 so that it is possible to perform an evaluation under conditions close to visual evaluation conditions. The distance between the CCD camera 6 and the sample (antiglare film) 3 is about 250 millimeters, for example. The CCD camera 6 is focused so that the matrix of the matrix filter 2 or 5 is sharply imaged. The diaphragm of the CCD camera 6 is adjusted to an appropriate position. It should be noted that the reason why measurement is carried out with an arrangement comprising a white light source, a matrix filter, a sample, and a CCD camera is to artificially reproduce the arrangement of a liquid crystal display on the assumption that the present invention is applied thereto.

Data obtained by photographing is taken into a computer 7. At this time, after the captured data of 8-bit gray scale has been checked, it is converted into data of 16-bit gray scale in order to prevent occurrence of a truncation error in computations performed in image processing. The captured data is subjected to image processing to obtain appropriate values for digitization. The image processing includes low-pass filtering, shading correction, and contrast enhancement. In the contrast enhancement, for example, contrast is set to 93, gamma to 30, and brightness to 48. If the luminance is excessively high or low with these settings, the diaphragm of the CCD camera 6 is adjusted appropriately, and measurement is carried out over again from the beginning. It is desirable that under these conditions the mean luminance should be of the order of 145 cd/m$^2$. In digitization of the intensity of scintillation, the dispersion of the luminance distribution is obtained as a standard deviation and expressed in the form of a standard deviation value. The performance of the sample is evaluated by comparing the obtained scintillation value with a predetermined value. It should be noted that because completely the same conditions cannot always be reproduced owing to changes in measurement environment (e.g. a stain on the matrix filter or undesired deflection of the light source), it is desirable to provide a standard sample and to make a correction based on a change in the scintillation value of the standard sample except when measurement is carried out continuously.

Figure 2:
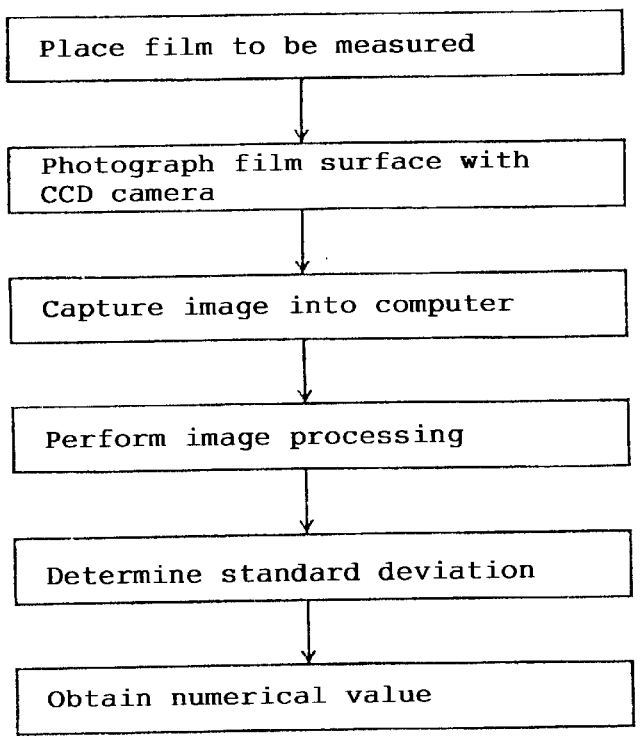
FIG. 2 is a flowchart showing a measuring process.
Figure 3A:
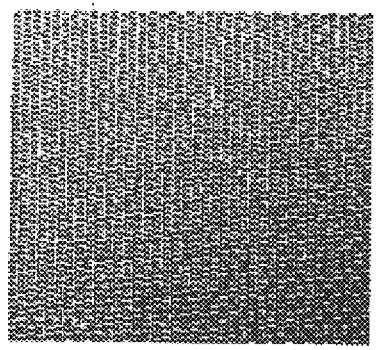
FIG. 3(a)–FIG. 3(d) are diagrams showing the contents of images in the measuring process in FIG. 2.
Figure 3B:
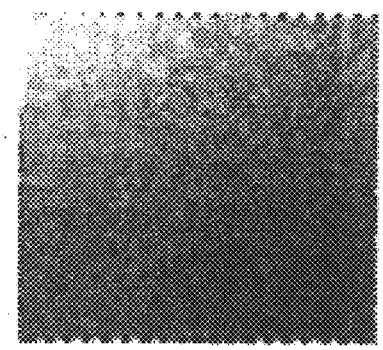
Figure 3C:
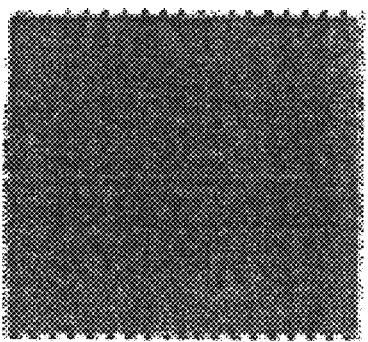
Figure 3D:
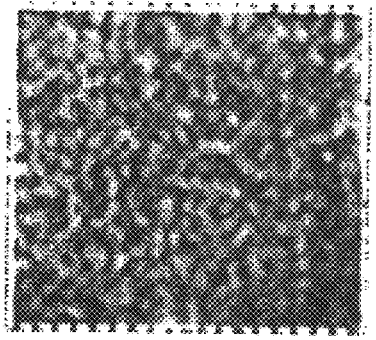
Figure 4A:
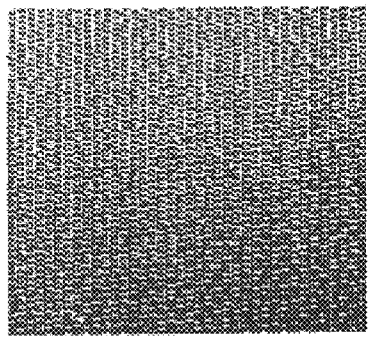
FIG. 4(a)–FIG. 4(d) are diagrams illustrating changes in luminance distribution caused by image processing.
Figure 4B:
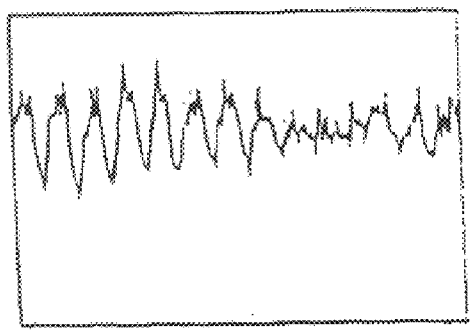
Figure 4C:
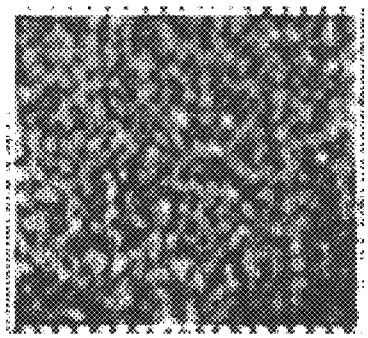
Figure 4D:
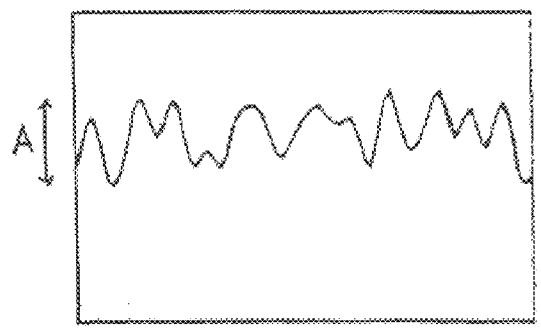
Figure 5A:
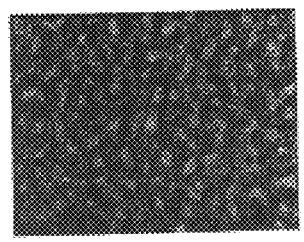
FIG. 5(a)–FIG. 5(d) are diagrams illustrating changes in luminance distribution when scintillation is small and when it is large.
Figure 5C:
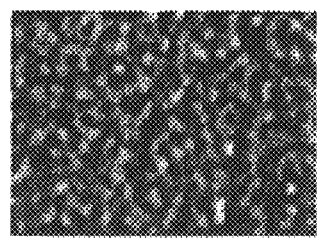
Figure 5B:
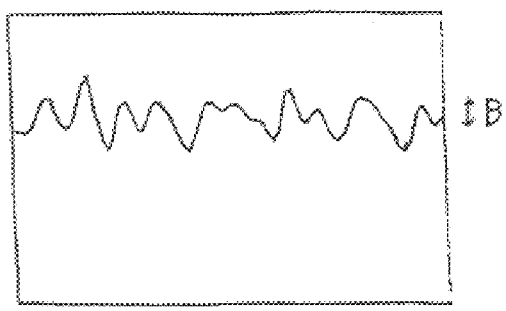
Figure 5D:
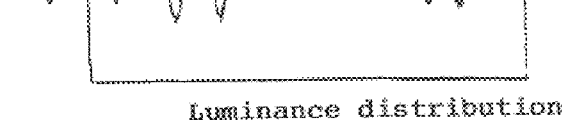

FIG. 2 is a flowchart showing the measuring process carried out with the apparatus shown in FIG. 1.

First, a film to be measured is placed on the matrix filter, and the film surface is photographed with the CCD camera. Next, image data obtained by photographing is taken into the computer to perform image processing.

FIG. 3 shows the contents of images under processing.

In the image processing, an area to be subjected to image processing is selected from the captured raw image. The reason for this is to perform image processing only for a portion of the sample where the antiglare film is stuck. Part (a) of FIG. 3 shows the raw image. In this image, luminance changes caused by the matrix of the matrix filter appear clearly.

Part (b) of FIG. 3 shows an image obtained by filtering the raw image to remove harmonics so that luminance changes due to the matrix of the matrix filter do not appear. The filtering is carried out to provide the same conditions as visual evaluation conditions from the point of view that when scintillation is visually evaluated, the matrix of the matrix filter cannot be recognized. The filtering is carried out by subjecting the raw image to low-pass filtering to such an extent that the matrix cannot be recognized. More specifically, low-pass filtering of the software used is applied to the raw image three times with a 7×7 kernel at 100%.

Next, the luminance is flattened. Part (c) of FIG. 3 shows an image obtained by making a luminance correction to the image shown in part (b) of FIG. 3. That is, shading correction is made to correct a luminance distribution produced because the light source per se has a planar distribution of luminance. The maximum point consists of 10 pixels.

Part (d) of FIG. 3 shows an image obtained as a result of contrast enhancement. Enhancement of contrast is not essential for digitization. However, contrast enhancement is performed to make the luminance distribution easy to see in evaluation of scintillation.

In the image processed as stated above, a standard deviation value of luminance is obtained for a part free from a luminance change due to a flaw of the matrix filter or the like. At this time, the area for image processing is moved from one region to another so that the mean value of luminance is approximately the same for each sample. The reason for this is that the mean value may differ for different regions because of the luminance distribution of the light source. When no appropriate mean value can be obtained wherever the image processing area is moved, the diaphragm of the CCD camera is varied.

FIG. 4 is a diagram illustrating changes in luminance distribution caused by image processing, which shows luminance distributions of the image before and after the image processing. In the illustrated example, the number of pixels is 160×120, and the actual size is 10 millimeters×7.5 millimeters.

Part (a) of FIG. 4 shows a captured raw image, and part (b) of FIG. 4 shows the luminance distribution of the raw image as captured. As will be understood from part (b) of FIG. 4, there are very fine changes in luminance because of the influence of the matrix of the matrix filter. By subjecting the raw image to the above-described image processing, an image as shown in part (c) of FIG. 4 is obtained. The luminance distribution of the image thus obtained is as shown in part (d) of FIG. 4. The magnitude A of changes in luminance shown in part (d) of FIG. 4 is data for determining a standard deviation.

FIG. 5 is a diagram illustrating luminance changes when scintillation is small and when it is large. Part (a) of FIG. 5 shows an image in which scintillation is small. The luminance distribution of this image is as shown in part (b) of FIG. 5. It will be understood from part (b) of FIG. 5 that changes B in luminance are extremely small. Part (c) of FIG. 5 shows an image in which scintillation is large. The luminance distribution of this image is as shown in part (d) of FIG. 5. It will be understood from part (d) of FIG. 5 that changes C in luminance are large.

The magnitudes B and C of changes in luminance are standard deviations. The standard deviation value is defined as a numerical value representing the intensity of scintillation. The larger the numerical value, the stronger the scintillation. The absolute numerical value of scintillation may differ for different measuring apparatuses (each comprising a light source, a matrix filter, and a CCD camera), image processing software programs and specific image processing methods. However, the correlation between the numerical values is maintained. If measurement is carried out with the same combination of a measuring apparatus, an image processing software program and an image processing method, it is possible to obtain numerical values with high reproducibility.

It should be noted that devices used for measurement in this example are as follows:

Optical apparatus:
  Mapping type evaluation apparatus; Model MJ-RTS (Mizojiri Optical Co., Ltd.)
  Transmission measuring mode
CCD light-receiving part:
  CCD camera (KP-M1)
  C-mount adapter (Nikon)
  Close-up ring (PK-11A; Nikon)
  Camera lens (50 mm, F1.4s NIKKOR)
Light source:
  LIGHTBOX 45 (HAKUBA)
Matrix filter:
  Pitch: 140 $\mu$m×170 $\mu$m; glass thickness: 1 mm
Image processing software:
  Windows 95 version of Image-Pro Plus 3.0 (Media Cybemetics)

FIG. 6 is a diagram showing the results of measurement at a mean luminance of 145 cd/m$^2$ of captured images. More specifically, FIG. 6 shows the results of measurement carried out by using a glossiness measuring apparatus (gloss 20°) and the results of a sensory test and further shows scintillation values obtained by the method according to the present invention.

In FIG. 6:

Sample 1: containing silica particles having a particle diameter of 1 to 2 micrometers (Ra=0.256; Sm=40.1)

Sample 2: containing silica particles having a particle diameter of 1 to 2 micrometers (Ra=0.186; Sm=30.2)

Sample 3: containing silica particles having a particle diameter of 1 to 2 micrometers (Ra=0.307; Sm=30.5)

Sample 4: containing silica particles having a particle diameter of 1 to 2 micrometers (Ra=0.385; Sm=29.7)

Sample 5: containing no particle (embossed) (Ra=0.102; Sm=31.1)

Sample 6: containing silica particles having a particle diameter of 3 micrometers (Ra=0.205; Sm=25.9)

Sample 7: containing silica particles having a particle diameter of 3 micrometers (Ra=0.264; Sm=23.7)

Sample 8: containing silica particles (Ra=0.323; Sm=36.2)

TAC: a transparent film (base film) not subjected to antiglare treatment.

In the above data, Ra is a numerical value expressed in units of micrometers, which is one (center line average roughness) of measurements representing surface roughness according to JIS (Japanese Industrial Standards), and Sm is a numerical value expressed in units of micrometers, which represents the distance between adjacent valleys of surface unevenness.

Measuring Methods:

[Gloss (20°)]

In conformity to JIS-S-Z-8741, the reverse side of a film was stuck on a holding plate (dull black) with double-coated adhesive tape, and measurement was carried out by using GM-26D, manufactured by Murakami Color Research Laboratory.

[Sensory Test]

A matrix filter was placed on a planar white light source (inspection viewer) in such a way that the processed surface of the filter faced the light source. An antiglare film was placed over the matrix filter in such a way that the antiglare-treated surface of the film faced upward. Then, with the film edges held with hands, scintillation was observed.

◎ . . . No visible scintillation

○ . . . Slight but inconspicuous scintillation

Δ . . . Conspicuous scintillation

X . . . Strong scintillation

In the case of the gloss (20°) measuring method, as the numerical value increases, the degree of scintillation is supposed to become higher. However, it will be understood from the results shown in FIG. 6 that some results of the gloss (20°) measuring method do not agree with the results of the sensory test. For example, for sample 1, sample 3, sample 4, sample 6, and sample 7, the results of the gloss (20°) measuring method relatively agree with those of the sensory test. However, for sample 2, sample 5, sample 8, and the base film, the results of the gloss (20°) measuring method do not agree with those of the sensory test. In contrast, the scintillation values obtained by the method according to the present invention agree with the results of the sensory test for all the samples. Furthermore, it is possible to judge the quality of an antiglare film in terms of scintillation characteristics by judging whether or not the scintillation value as measured at a mean luminance of 145 cd/m$^2$ of the captured image is greater than 15.

As has been stated above, according to the present invention, the luminance distribution is measured, and after image processing has been performed, the standard deviation of the luminance distribution is defined as a scintillation value. Thus, scintillation can be digitized so that the resulting scintillation value approximately agrees with the result of a sensory test. Accordingly, the present invention is extremely useful for development of antiglare films and so forth.

It should be noted that the present invention is not necessarily limited to the foregoing embodiments but can be modified in a variety of ways without departing from the gist of the present invention.

What is claimed is:

1. A method of quantitatively evaluating scintillation, comprising the steps of:
   making light from a white light source incident on a surface of an object to be measured through a matrix filter;
   photographing reflected light or transmitted light from said object and capturing the light as data;
   performing image processing for a luminance distribution of the captured light to obtain a standard deviation of dispersion of the luminance distribution; and
   defining a value of the obtained standard deviation as a scintillation value of the surface of said object.

2. A method of quantitatively evaluating scintillation according to claim 1, wherein said object is an antiglare film.

3. A method of quantitatively evaluating scintillation according to claim 1 or 2, wherein performance of said object is evaluated by judging whether or not the scintillation value is greater than a predetermined value.

4. A method of quantitatively evaluating scintillation according to claim 3, wherein said predetermined value for the scintillation value is 15 when the scintillation value is measured at a mean luminance of 145 cd/m$^2$ of a captured image.

5. An apparatus for quantitatively evaluating scintillation, comprising:
   a white light source;
   a matrix filter;
   a photographing device; and
   a computer;
   wherein light from said white light source is made incident on a surface of an object to be measured through said matrix filter, and reflected light or transmitted light from said object is photographed with said photographing device and captured as data, and further said data is processed by said computer to obtain a standard deviation of dispersion of a luminance distribution, and a value of the standard deviation obtained is defined as a scintillation value of the surface of said object.

6. An apparatus for quantitatively evaluating scintillation according to claim 5, wherein said photographing device is a CCD camera.

7. An apparatus for quantitatively evaluating scintillation according to claim 5 or 6, wherein said object is an antiglare film.

8. An apparatus for quantitatively evaluating scintillation according to either of claims 5 and 6, wherein performance of said object is evaluated by judging whether or not the scintillation value is greater than a predetermined value.

9. An apparatus for quantitatively evaluating scintillation according to claim 8, wherein said predetermined value for the scintillation value is 15 when the scintillation value is measured at a mean luminance of 145 cd/M$^2$ of a captured image.

* * * * *